United States Patent [19]

Knaus et al.

[11] Patent Number: 4,468,403

[45] Date of Patent: Aug. 28, 1984

[54] ANALGESIC SUBSTITUTED PIPERIDYLIDENE-2-SULFON(CYAN)AMIDE DERIVATIVES

[75] Inventors: Edward E. Knaus, Edmonton; Brent K. Warren, Calgary; Theodore A. Ondrus, Edmonton, all of Canada

[73] Assignee: Canadian Patents & Development Limited, Ottawa, Canada

[21] Appl. No.: 399,994

[22] Filed: Jul. 20, 1982

[51] Int. Cl.³ .................. A61K 31/445; C07D 401/12; C07D 211/72

[52] U.S. Cl. .................... 424/267; 546/193; 546/194; 546/216; 546/221; 546/223; 546/224; 546/242; 546/244

[58] Field of Search .............. 546/193, 194, 216, 221, 546/223, 224, 242, 244; 424/267

[56] References Cited

U.S. PATENT DOCUMENTS 4,055,561 10/1977 Grisar et al. .................... 546/223 X

OTHER PUBLICATIONS

Abramovitch, R. et al., *J. Org. Chem.*, 37(12), 2022, (1972).
McKillip, W. et al., *Chem. Rev.*, 73, 255, (1973).
Knaus, E. et al., *J. Met. Chem.*, 13, 481, (1976).
Knaus, E. et al., *Can. J. Chem.*, 58, 2447, (1980).
Ritchie, A. et al., *J. Chem. Soc.*(c), 1968, (3), 227–228.
*Chemical Abstracts*, 69:96401e, (1968), [Dalla Croce, P., et al., *Rend. Ist. Lombardo Sci. Lett.*, A. 1967, 101(4), 680–691].
Fieser, L. et al., *Reagents for Organic Synthesis*, vol. 1, John Wiley, New York, 1967, p. 95.

March, J., *Advanced Organic Chemistry*, McGraw Hill, New York, 1968, pp. 350–351 and 897.
*Chemical Abstracts*, 94:174934p, (1981), [Warren, B. et al., *J. Med. Chem.* 1981, 24(4), 462–464].

*Primary Examiner*—Richard A. Schwartz
*Attorney, Agent, or Firm*—Alan A. Thomson

[57] ABSTRACT

Pharmaceutical compounds of the general formula (1) have been prepared

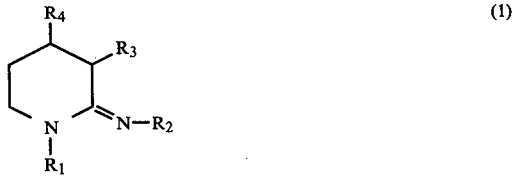

and non-toxic pharmaceutically acceptable salts thereof, wherein $R_1$ is a lower alkyl, phenyl lower alkyl, amino substituted phenyl lower alkyl, nitro substituted phenyl lower alkyl, cycloalkyl lower alkyl or a lower alkenyl substituent, $R_2$ is a member selected from the group consisting of a cyano, pyridylsulfonyl, lower alkyl substituted sulfonyl, phenylsulfonyl, lower alkyl substituted phenylsulfonyl, lower alkoxy substituted phenylsulfonyl, halogen substituted phenylsulfonyl, nitro substituted phenylsulfonyl, amino substituted phenylsulfonyl and lower alkyl amido substituted phenylsulfonyl; $R_3$ is a hydrogen or halogen atom; and $R_4$ is a hydrogen, lower alkyl or lower alkoxy substituent, lower denoting a straight or branched chain having from 1-4 carbon atoms. These compounds exhibit analgesic agonist activity or analgesic agonist-antagonist activities.

38 Claims, No Drawings

ANALGESIC SUBSTITUTED PIPERIDYLIDENE-2-SULFON(CYAN)AMIDE DERIVATIVES

The present invention relates to pharmaceutical compounds. More particularly, the invention provides novel 1-alkyl(arylalkyl,cycloalkylalkyl,alkenyl)-piperidylidene-2-sulfon(cyan)amide derivatives or non-toxic pharmaceutically acceptable salts thereof having useful physiological effects, particularly analgesic properties. The invention relates to such compounds and compositions thereof, and to processes for making and using them.

In the course of studies of various pyridine and piperidine derivatives, our group previously had prepared certain 7-substituted 2,7-diazabicyclo[4.1.0]hept-4-enes and -hept-3-enes, which were found to exhibit significant analgesic and antiprotozoal activities. See J. Med. Chem. 24, 462–464, 1981, B. K. Warren et al. Others have found 1,2,4,5-tetraalkyl-4-arylpiperidines to have analgesic activity (see U.S. Pat. No. 4,284,635, Aug. 18, 1981, Zimmerman).

DESCRIPTION OF THE INVENTION

The novel 1-alkyl(arylalkyl,cycloalkylalkyl,alkenyl)-piperidylidene -2-sulfon(cyan)amide derivatives have been prepared which have the structural formula (1):

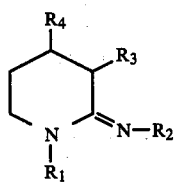
(1)

and non-toxic pharmaceutically acceptable salts thereof, wherein $R_1$ is a lower alkyl, phenyl lower alkyl, amino substituted phenyl lower alkyl, nitro substituted phenyl lower alkyl, cycloalkyl lower alkyl or lower alkenyl substituent, $R_2$ is a member selected from the group consisting of cyano, pyridylsulfonyl, lower alkyl substituted sulfonyl, phenylsulfonyl, lower alkyl substituted phenylsulfonyl, lower alkoxy substituted phenylsulfonyl, halogen substituted phenylsulfonyl, nitro substituted phenylsulfonyl, amino substituted phenylsulfonyl and lower alkyl amido substituted phenylsulfonyl; $R_3$ is a hydrogen or halogen substituent; and $R_4$ is a hydrogen, lower alkyl or lower alkoxy substituent. In this specification, it will be understood that "lower alkyl" and "lower alkoxy" substituents mean those having from 1 to 4 carbons atoms, and "halogen" means fluorine, chlorine, bromine or iodine. These compounds exhibit analgesic activity. Non-toxic pharmaceutically acceptable salts are also within the scope of the present invention.

These 1-alkyl(arylalkyl,cycloalkylalkyl,alkenyl)-piperidylidene-2-sulfon(cyan)amide derivatives are prepared by reacting in an inert solvent, an azide of the formula (2):

$$R_2-N_3 \qquad (2)$$

wherein $R_2$ is a member selected from the group consisting of cyano, pyridylsulfonyl, lower alkyl substituted sulfonyl, phenylsulfonyl, lower alkyl substituted phenylsulfonyl, lower alkoxy substituted phenylsulfonyl, halogen substituted phenylsulfonyl, nitro substituted phenylsulfonyl, amino substituted phenylsulfonyl and lower alkylamido substituted phenylsulfonyl, with a 1-alkyl(arylalkyl,cycloalkylalkyl,alkenyl)-1,2,3,4-tetrahydropyridine of structural formula (3):

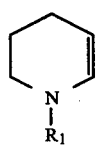
(3)

wherein $R_1$ is a lower alkyl, phenyl lower alkyl, amino substituted phenyl lower alkyl, nitro substituted phenyl lower alkyl, cycloalkyl lower alkyl or lower alkenyl substituent, allowing the reaction to occur (normally at room temperature) with evolution of nitrogen gas to convert to 1-alkyl(arylalkyl,cycloalkylalkyl,alkenyl)-piperidylidene-2-sulfon (cyan)amides of the formula (4):

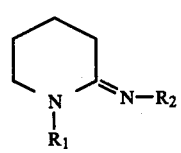
(4)

wherein $R_1$ and $R_2$ are as defined above. These reactions can take place in inert organic solvents, such as ether, tetrahydrofuran, chloroform, benzene, toluene, hexane, etc. Compounds of formula (1) having a $R_3$-substituent other than hydrogen are obtained by reaction of compounds having formula (4) with an organolithium base such as n-butyllithium to afford an anion of formula (5):

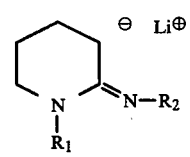
(5)

which on reaction with electrophilic reagents (such as N-halosuccinimides) are converted to compounds of formula (1) having a $R_3$-substituent (such as the halogens).

Amino substituted phenylsulfonyl compounds of formula (1) are also obtained by reduction of the corresponding nitro substituted phenylsulfonyl derivatives (1) using a suitable reducing agent, such as palladium on charcoal, platinum oxide, or the equivalent. Hydroxylic solvents such as methanol, ethanol and propanol are most suitable for this reaction.

Compounds of formula (1) can also be obtained by reacting an azide of the formula (2) wherein $R_2$ is defined as above, with a 1-alkyl-1,2-dihydropyridine of structural formula (6):

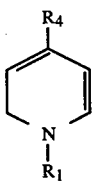

wherein $R_1$ is a lower alkyl substituent and $R_4$ is a member selected from the group consisting of hydrogen, lower alkyl or lower alkoxy, allowing the reaction to occur (most suitably at room temperature) with evolution of nitrogen gas to convert to 2-alkyl-2,7-diazabicyclo[4.1.0]-hept-4-ene of structural formula (7):

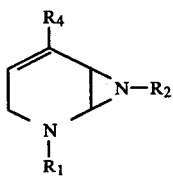

which on reduction using a suitable reducing agent, e.g. Pd on charcoal with $H_2$ gas, is converted to compounds of formula (1) wherein $R_3$ is hydrogen and $R_1$, $R_2$ and $R_4$ are as defined above. An alcohol solvent has been found most suitable.

Alternatively, compounds of formula (1) can also be prepared by reacting an azide of the formula (2) wherein $R_2$ is defined as above, with a 1-alkyl-1,4-dihydropyridine derivative of structural formula (8):

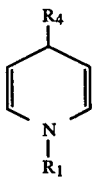

wherein $R_1$ is a lower alkyl group and $R_4$ is a hydrogen, lower alkyl or lower alkoxy substituent, allowing the reaction to occur (e.g. at room temperature) with evolution of nitrogen gas to convert to a 2-alkyl-2,7-diazabicyclo[4.1.0]hept-3-ene of structural formula (9):

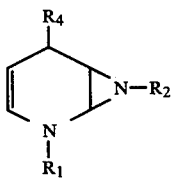

which on reduction using a suitable reducing agent, is converted to compounds of structural formula (1) wherein $R_3$ is hydrogen, $R_1$, $R_2$ and $R_4$ are as defined above.

More particularly, the following compounds have been prepared, and through testing, have been found to have analgesic agonist activity.

| Name | Designation |
|---|---|
| 1-Methylpiperidylidene-2-methanesulfonamide | W-1 |
| 1-Methylpiperidylidene-2-benzenesulfonamide | W-2 |
| 1-Methylpiperidylidene-2-(4-chlorophenyl)sulfonamide | W-3 |
| 1-Methylpiperidylidene-2-(4-methoxyphenyl)sulfonamide | W-4 |
| 1-Methylpiperidylidene-2-(4-methylphenyl)sulfonamide | W-5 |
| 1-Methylpiperidylidene-2-(4-nitrophenyl)sulfonamide | W-6 |
| 1-Methylpiperidylidene-2-(3-nitrophenyl)sulfonamide | W-7 |
| 1-Methylpiperidylidene-2-(2-nitrophenyl)sulfonamide | W-8 |
| 1-Methylpiperidylidene-2-(4-aminophenyl)sulfonamide | W-9 |
| 1-Methylpiperidylidene-2-(3-aminophenyl)sulfonamide | W-10 |
| 1-Methylpiperidylidene-2-(2-aminophenyl)sulfonamide | W-11 |
| 1-Methylpiperidylidene-2-(4-acetamidophenyl)sulfonamide | W-12 |
| 1-Methylpiperidylidene-2-cyanamide | W-13 |
| 1-Methylpiperidylidene-2-(3-pyridyl)sulfonamide | W-14 |
| 1-Phenylethylpiperidylidene-2-(4-chlorophenyl)sulfonamide | W-15 |
| 1-Phenylethylpiperidylidene-2-(4-aminophenyl)sulfonamide | W-16 |
| 1-Phenylethylpiperidylidene-2-(3-pyridyl)sulfonamide | W-17 |
| 1-(4-Nitrophenylethyl)piperidylidene-2-(4-chlorophenyl)sulfonamide | W-18 |
| 1-(4-Aminophenylethyl)piperidylidene-2-(4-chlorophenyl)sulfonamide | W-19 |
| 3-Bromo-1-methylpiperidylidene-2-cyanamide | 0-1 |
| 1,4-Dimethylpiperidylidene-2-cyanamide | 0-2 |
| 4-Ethoxy-1-methylpiperidylidene-2-cyanamide | 0-3 |

More particularly, the following compounds have also been prepared, and through testing, have been found to have analgesic agonist and analgesic antagonist activity.

| Name | Designation |
|---|---|
| 1-Cyclopropylmethylpiperidylidene-2-(4-chlorophenyl)sulfonamide | W-20 |
| 1-Cyclopropylmethylpiperidylidene-2-(4-aminophenyl)sulfonamide | W-21 |
| 1-Cyclopropylmethylpiperidylidene-2-(3-pyridyl)sulfonamide | W-22 |
| 1-Cyclobutylmethylpiperidylidene-2-(4-chlorophenyl)sulfonamide | W-23 |
| 1-Cyclobutylmethylpiperidylidene-2-(4-aminophenyl)sulfonamide | W-24 |
| 1-Cyclobutylmethylpiperidylidene-2-(3-pyridyl)sulfonamide | W-25 |
| 1-n-Propylpiperidylidene-2-(4-chlorophenyl)sulfonamide | W-26 |
| 1-n-Propylpiperidylidene-2-(4-aminophenyl)sulfonamide | W-27 |
| 1-n-Propylpiperidylidene-2-(3-pyridyl)sulfonamide | W-28 |
| 1-Isobutylpiperidylidene-2-(4-chlorophenyl)sulfonamide | W-29 |
| 1-Isobutylpiperidylidene-2-(4-aminophenyl)sulfonamide | W-30 |
| 1-Isobutylpiperidylidene-2-(3-pyridyl)sulfonamide | W-31 |
| E-1-(1-Propenyl)piperidylidene-2-(4-chlorophenyl)sulfonamide | W-32 |

Suitable pharmaceutically acceptable salt forms of these compounds include alkaline metal salts, for example, the potassium or sodium salt, and the ammonium salt, and alkaline earth metal salts, e.g. the calcium or Mg salt, as well as the mineral acid salts, for example, the hydrochloride and hydrobromide salts.

These compounds can be administered either parenterally, as by injection, or orally. As a liquid carrier, a carrier such as water, ethyl alcohol or polyethylene glycol, or other physiologically acceptable solvents or dispersing liquids can be used. For oral administration, either solid or liquid carriers may be used. One commonly used solid carrier is gum acacia, but others are also suitable. An operative dosage range is between about 0.000001 and 200 mg/kg, preferably between 0.001 and 10 mg/kg.

The following non-limitative examples illustrate some selected methods for producing the compounds according to the present invention, as well as comparative data illustrating the analgesic effect of representative compounds according to the present invention.

The starting materials for the preparation of the compounds of formula (1), viz., the azides of formula (2), 1-alkyl(arylalkyl,cycloalkylalkyl,alkenyl)-1,2,3,4-tetrahydropyridine of formula (3), 1-alkyl-1,2-dihydropyridines of formula (6) and 1-alkyl-1,4-dihydropyridines of formula (8) are either known or are conveniently prepared from known starting materials by methods known per se.

PREPARATION

Example 1

1-methylpiperidylidene-2-methanesulfonamide (W-1)

(See schematic representation of reaction)

A solution of methanesulfonyl azide (0.377 g, 3.14 mmol) in 10 ml of ether was added to a solution of 1-methyl-1,2,3,4-tetrahydropyridine (0.305 g, 3.4 mmol) in 10 ml of ether with stirring at 25° C. Evolution of nitrogen gas was immediate. The reaction was allowed to proceed for one hour at room temperature. The solid which precipitated was removed by filtration and recrystallized from methylene chlorideether to give 1-methylpiperidylidene-2-methanesulfonamide (0.492 g, 82%) as a white solid with mp 129–131° C., IR (KBr) 1590 cm$^{-1}$ (C+N); NMR(CDCl$_3$) 1.69–1.98 (m, 4H, H-4 and H-5), 2.9–3.25 (m, 2H, H-3), 3.02 (s, 3H, Me), 3.06 (s, 3H, Me), 3.24–3.53 (m,2H, H-6).

Analysis found: C, 44.04; H, 7.19; N, 14.86. C$_7$H$_{14}$N$_2$O$_2$S requires: C 44.19; H, 7.42; N, 14.72.

SCHEMATIC FOR EXAMPLE 1

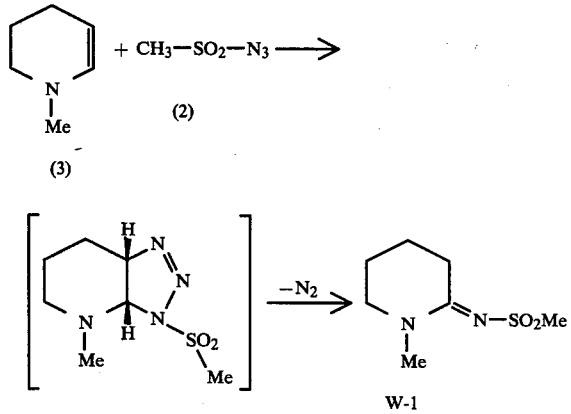

Example 2

Related 1-alkyl(arylalkyl,cycloalkylalkyl,alkenyl)-piperidylidene-2-sulfon(cyan)amide derivatives have been prepared as shown in the schematic representation below using equivalent quantities of other azides of formula (2) using a procedure similar to that outlined in Example 1.

The melting point for each product is set out in Table 1.

Schematic for Example 2

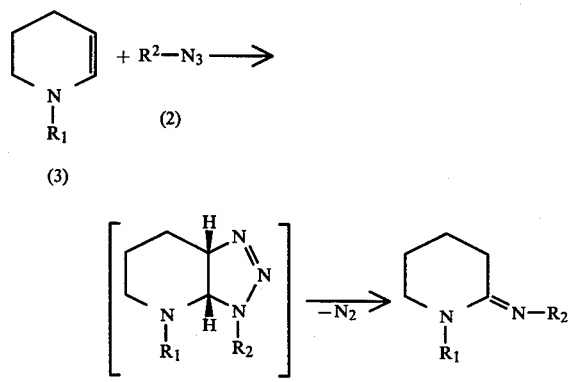

Example 3

1-methylpiperidylidene-2-(3-aminophenyl)sulfonamide (W-10)

(see schematic representation following example)

10% Palladium on charcoal (30 mg) was added at once and then 0.5 ml of 85% hydrazine hydrate was added dropwise to a suspension of 1-methylpiperidylidene-2-(3-nitrophenyl)-sulfonamide (0.20 g, 0.67 mmol) in 30 ml 95% ethyl alcohol with stirring at 0° C. The temperature of the reaction mixture was allowed to return to 25° C. and the reaction mixture was stirred for a further 16 hours. The solid material was removed by filtration. Water (50 ml) was added to the filtrate which was then extracted with methylene chloride (5×50 ml). Drying (Na$_2$SO$_4$) and removal of the solvent in vacuo gave 1-methylpiperidylidene-2-(3-amino-phenyl)sulfonamide as a pale yellow solid which was then recrystallized from carbon tetrachloride-acetone to give yellow crystals with mp 164–165° (0.137 g, 76%); IR (KBr) 3480 and 3370 (NH$_2$) and 1590 cm$^{-1}$ (C=N).

TABLE 1

| | 1-alkyl(arylalkyl, cycloalkylalkyl, alkenyl)piperidylidene-2-sulfon(cyan)amides prepared according to Example 2 | | | |
|---|---|---|---|---|
| Chemical Name | Designation | R$_1$ | R$_2$ | MP |
| 1-Methylpiperidylidene-2-benezenesulfonamide | W-2 | Me | —SO$_2$—C$_6$H$_5$ | 103–104° |
| 1-Methylpiperidylidene-2-(4-chlorophenyl)sulfonamide | W-3 | Me | —SO$_2$—C$_6$H$_4$—4-Cl | 106–107° |
| 1-Methylpiperidylidene-2-(4-methoxyphenyl)sulfonamide | W-4 | Me | —SO$_2$—C$_6$H$_4$—4-OMe | 103–105° |
| 1-Methylpiperidylidene-2- | W-5 | Me | —SO$_2$—C$_6$H$_4$—4-Me | 110–111° |

TABLE 1-continued 1-alkyl(arylalkyl, cycloalkylalkyl, alkenyl)piperidylidene-2-sulfon(cyan)amides prepared according to Example 2

| Chemical Name | Designation | R₁ | R₂ | MP |
|---|---|---|---|---|
| 1-Methylpiperidylidene-2-(4-methylphenyl)sulfonamide | W-6 | Me | $-SO_2-C_6H_4-4-NO_2$ | 146–148° |
| 1-Methylpiperidylidene-2-(3-nitrophenyl)sulfonamide | W-7 | Me | $-SO_2-C_6H_4-3-NO_2$ | 136–137° |
| 1-Methylpiperidylidene-2-(2-nitrophenyl)sulfonamide | W-8 | Me | $-SO_2-C_6H_4-2-NO_2$ | 126–127° |
| 1-Methylipiperidylidene-2-(4-aminophenyl)sulfonamide | W-9 | Me | $-SO_2-C_6H_4-4-NH_2$ | 186–188° |
| 1-Methylpiperidylidene-(4-acetamidophenyl)sulfonamide | W-12 | Me | $-SO_2-C_6H_4-4-NHCOMe$ | 221–223° |
| 1-Methylpiperidylidene-2-cyanamide | W-13 | Me | CN | 97–98° |
| 1-Methylpiperidylidene-2-(3-pyridyl)sulfonamide | W-14 | Me | $-SO_2-$3-pyridyl | 96–97° |
| 1-Phenylethylpiperidylidene-2-(4-chlorophenyl)sulfonamide | W-15 | $C_6H_5(CH_2)_2$ | $-SO_2-C_6H_4-4-Cl$ | 110–111° |
| 1-Phenylethylpiperidylidene-2-(4-aminophenyl)sulfonamide | W-16 | $C_6H_5(CH_2)_2$ | $-SO_2-C_6H_4-4-NH_2$ | 170–171° |
| 1-Phenylethylpiperidylidene-2-(3-pyridyl)sulfonamide | W-17 | $C_6H_5(CH_2)_2$ | $-SO_2-$3-pyridyl | 105–106° |
| 1-Cyclopropylmethylpiperidylidene-2-(4-chlorophenyl)sulfonamide | W-20 | ▷-CH₂- | $-SO_2-C_6H_4-4-Cl$ | 114.5–115.5° |
| 1-Cyclopropylmethylpiperidylidene-2-(4-aminophenyl)sulfonamide | W-21 | ▷-CH₂- | $-SO_2-C_6H_4-4-NH_2$ | 164.5–165° |
| 1-Cyclopropylmethylpiperidylidene-2-(3-pyridyl)sulfonamide | W-22 | ▷-CH₂- | $-SO_2-$3-pyridyl | 88.5–89° |
| 1-Cyclobutylmethylpiperidylidene-2-(4-chlorophenyl)sulfonamide | W-23 | ☐-CH₂- | $-SO_2-C_6H_4-4-Cl$ | 113–113.5° |
| 1-Cyclobutylmethylpiperidylidene-2-(4-aminophenyl)sulfonamide | W-24 | ☐-CH₂- | $-SO_2-C_6H_4-4-NH_2$ | 216–217° |
| 1-Cyclobutylmethylpiperidylidene-2-(3-pyridyl)sulfonamide | W-25 | ☐-CH₂- | $-SO_2-$3-pyridyl | 55–57° |
| 1-n-Propylpiperidylidene-2-(4-chlorophenyl)sulfonamide | W-26 | $CH_3(CH_2)_2$ | $-SO_2-C_6H_4-4-Cl$ | 107–108° |
| 1-n-Propylpiperidylidene-2-(4-aminophenyl)sulfonamide | W-27 | $CH_3(CH_2)_2$ | $-SO_2-C_6H_4-4-NH_2$ | 178–179° |
| 1-n-Propylpiperidylidene-2-(3-pyridyl)sulfonamide | W-28 | $CH_3(CH_2)_2$ | $-SO_2-$3-pyridyl | 109–110° |
| 1-Isobutylpiperidylidene-2-(4-chlorophenyl)sulfonamide | W-29 | $Me_2-CH-CH_2-$ | $-SO_2-C_6H_4-4-Cl$ | 105–106° |
| 1-Isobutylpiperidylidene-2-(4-aminophenyl)sulfonamide | W-30 | $Me_2-CH-CH_2-$ | $-SO_2-C_6H_4-4-NH_2$ | 184–185° |
| 1-Isobutylpiperidylidene-2-(3-pyridyl)sulfonamide | W-31 | $Me_2-CH-CH_2-$ | $-SO_2-$3-pyridyl | 65–67° |
| E-1-(1-Propenyl)piperidylidene-2-(4-chlorophenyl)sulfonamide | W-32 | H\\C=C/ / Me / \\H | $-SO_2-C_6H_4-4-Cl$ | 106–107° |

Analysis found: C, 53.60; H, 6.33; N, 15.59.
$C_{12}H_{15}N_3O_2S$ requires: C, 53.91; H, 6.42; N, 15.72.

Schematic for Example 3

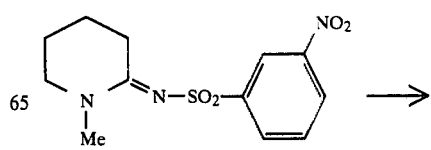

W-7

-continued

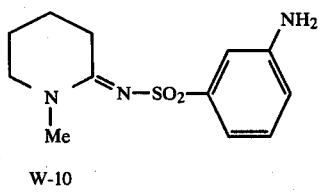

W-10

A similar reduction of 1-methylpiperidylidene-2-(2-nitrophenyl)sulfonamide gave 1-methylpiperidylidene-2-(2-aminophenyl)sulfonamide, mp 113–114° (Compound W-11).

Example 4

3-bromo-1-methylpiperidylidene-2-cyanamide (0-1)

n-butyllithium (2.03 mmol) in hexane (0.83 ml) was added to a suspension of 1-methylpiperidylidene-2-cyanamide (0.274 g) W-13 in 50 ml dry tetrahydrofuran at −77° C. under an atmosphere of nitrogen with stirring. The resulting solution was allowed to stir for 10 minutes at −77° C. This solution of 3-lithio-1-methyl-piperidylidene-2-cyanamide was then added dropwise over 20 min. to a solution of N-bromosuccinimide (0.356 g, 2.0 mmol) in 50 ml dry tetrahydrofuran at −77° C. with stirring under a nitrogen atmosphere. The reaction mixture was allowed to return to 25° C. slowly and water (50 ml) was added. Extraction with methylene chloride (3×75 ml), drying the extract (Na$_2$SO$_4$) and removal of the solvent in vacuo gave 0.364 g of a pale yellow solid. Purification was effected on six 8×8 in silica gel G plates, 0.75 mm in thickness, using methylene chloride-methanol (15:1 v/v) as development solvent. Extraction of the band having Rf 0.67 using warm methanol gave 3-bromo-1-methylpiperidylidene-2-cyanamide as a white solid with mp 116–118° (0.215 g, 66%); IR (KBr) 2160 (C≡N) and 1600 cm$^{-1}$ (C═N); NMR (CDCl$_3$) 1.72–2.38 (m, 4H, H-4 and H-5), 3.12 (s, 3H, Me), 3.56 (m, 2H, H-6) and 5.11 (m, 1H, H-3).

Mass spectrum (70 ev): Mass calc'd for C$_7$H$_{10}$N$_3$ $^{81}$Br: 217.0039.
Found: 217.0023.

Example 5

1,4-dimethylpiperidylidene-2-cyanamide (0-2)

(See schematic representation following example)

A solution of 1,4-dimethyl-1,2-dihydropyridine (9.69 g, 65 mmol) in ether (10 ml) was added slowly with stirring at 0° C. to a solution of cyanogen azide (5.1 g, 75 mmol). The reaction mixture was allowed to return to 25° C. and the solvent was removed in vacuo to give a reddish-brown product which was partitioned between 200 ml methylene chloride-water (1:1 v/v). The methylene chloride extract was dried (MgSo$_4$) and the solvent removed in vacuo to give 7-cyano-2,5-dimethyl-2,7-diazabicyclo [4.1.0]hept-4-ene (7.39 g, 76.2%) as a tan solid with mp 117° C. 10% palladium on charcoal (400 mg) was added to a solution of 7-cyano-2,5-dimethyl-2,7-diazabicyclo[4.1.0]hept-4-ene (2.23 g, 15 mmol) in 50 ml methanol and the reduction was effected using 10% palladium on charcoal and hydrogen gas at 35 psi for 24 hours. Filtration and then removal of the solvent in vacuo gave 1,4-dimethylpiperidylidene-2-cyanamide as a white solid (2.26 g, 99.8%) with mp 94° C; IR (KBr) 2180 (C≡N) and 1598 cm$^{-1}$ (C═N); NMR (CDCl$_3$) 3.44 (m, 2H, H-6), 3.05 (s, 3H, N—Me), 2.9 (m, 1H, H-3), 2.35 (m, 1H, H-3), 2.15-1.2 (m, 3H, H-4, H-5), 1.04 (d, J=5Hz, 3H, C-4 Me). Mass spectra (70 ev): Mass calc'd for C$_8$H$_{13}$N$_3$: 151,1109; found: 151.1107.

Schematic for Example 5

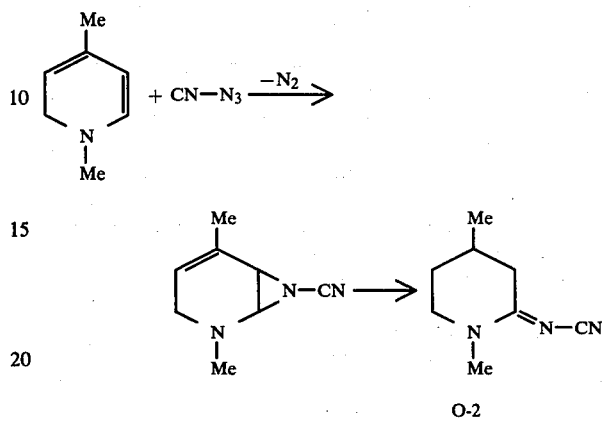

O-2

A similar reaction sequence employing 1-methyl-4-ethoxy-1,2-dihydropyridine gave 4-ethoxy-1-methyl-piperdylidene-2-cyanamide (Compound O-3).

Example 6

1-methylpiperidylidene-2-(4-aminophenyl)sulfonamide (W-9)

A solution of 4-aminobenzenesulfonyl azide (0.63 g, 3.2 mmol) in 75 ml ether was added slowly to a solution of 1-methyl-1,4-dihydropyridine (0.30 g, 3.2 mmol) in 75 ml ether with stirring at 25° C. Evolution of nitrogen gas was immediate. The reaction was allowed to proceed for 2 hours and the solvent was removed in vacuo to give 2-methyl-7-[(4-aminophenyl)sulfonyl]-2,7-diazabicyclo[4.1.0]hept-3-ene (0.82 g, 97%) with mp 188–190° . Hydrogenation of 2-methyl-7-[(4-aminophenyl) sulfonyl]-2,7-diazbicyclo[4.1.0]hept-3-ene (33 mg, 0.117 mmol) in 15 ml ethanol was effected using 10% palladium on charcoal (15 mg) and hydrogen gas at 30 psi for 4 hours. Removal of the catalyst by filtration and evaporation of the solvent in vacuo gave 1-methyl-piperidylidene-2-(4-aminophenyl)sulfonamide (31 mg, 93%) with mp 186-188° ; IR (KBr) 3480 and 3380 cm$^{-1}$ (NH$_2$) and 1590 cm$^{-1}$ (C═N).

Analysis found: C, 53.49; H, 6.24; N, 15.64. C$_{12}$H$_{15}$N$_3$O$_2$S requires:
C, 53.91; H, 6.42; N, 15.72.

Example 7

1-(4-nitrophenylethyl)piperidylidene-2-(4-chlorophenyl)sulfonamide (W-18)

A mixture of 1-phenylethylpiperdylidene-2-(4-chlorophenyl)sulfonamide (1.17 g, 3.11 mmol) W-15, 90% fuming nitric acid (3.0 ml) and concentrated nitric acid (2.0 ml) were stirred vigorously for 4 hours at 25° C. This mixture was poured onto 50 ml water and the pH adjusted to 10 using 1 N sodium hydroxide. Extraction with methylene chloride (4×50 ml), drying (Na$_2$SO$_4$) and removal of the solvent in vacuo gave a yellow gum which was purified by preparative tlc using 0.75 mm silica gel G plates with acetone: ether (1:1 v/v) as development solvent. Extraction of the band having R$_f$ 0.88 gave 1-(4-nitrophenylethyl)piperidylidene-2-(4- chlorophenyl)sulfonamide as a pale yellow solid (0.734 g, 61%) having mp 157°-158°; IR (KBr) 1350 and 1540 cm$^{-1}$ (NO$_2$).

EXAMPLE 8

1-(4-aminophenylethyl)piperidylidene-2-(4-chlorophenyl)sulfonamide (W-19)

10% palladium on charcoal (30mg) and then 85% hydrazine hydrate (0.5 ml) was added to a rapidly stirred suspension of 1-(4-nitrophenylethyl)piperidylidene-2-(4-chlorophenyl)sulfonamide (0.15 g, 0.355 mmol) W-18 in 95% ethanol (30 ml). The reaction was allowed to proceed for 4 hours at 25° C., the reaction mixture was filtered to remove the palladium on charcoal and water (30 ml) was added. Extraction with methylene chloride (3×30 ml), drying (Na$_2$SO$_4$) and removal of the solvent in vacuo gave a solid which on recrystallization from acetone/hexane gave 1-(4-aminophenylethyl)piperidylidene-2-(4 -chlorophenyl)sulfonamide (0.095 g, 68%) having mp 129°-130°, IR (KBr) 3370 and 3440 cm$^{-1}$ (NH$_2$).

ANALGESIC AGONIST TESTING

Analgesic activity was evaluated by the phenylquinone writhing test (H.O. Collier, L.C. Dineen, C. A. Johnson and C. Schneider, Br. J. Pharmacol. Chermotherap., 32, 295, 1968. Five male Swiss albino mice weighing 18-22 g were used in each group. The test compound, suspended in a solution of physiological saline and Tween 80 (TM) surfactant, was administered subcutaneously, and 30 min. later each mouse received a 0.03% phenyl-p-benzoquinone solution in a volume of 0.1 mL/10 g of body weight intraperitoneally. The total number of writhes exhibited by each animal in the test group was recorded and compared to that of a vehicle treated control group. The percent change is calculated according to the following equation: % change=100−(no. of writhes in treated group/no. of writhes in control group)×100. A compound causing a 30-50% reduction is considered to be slightly active, whereas one causing a greater than 50% reduction in the number of writhes is an active analgesic agent. The test results are shown in Table 2 and Table 3, the compounds tested being compared to Aspirin (TM), Dextropropoxyphene (TM), and morphine sulfate.

Compounds W-20 to W-32, inclusive, exhibited analgesic antagonist activity toward compounds W-1 to W-19, inclusive, 0-1 to 0-3, inclusive, as well as toward morphine sulfate. Naloxone (TM) also acted as an antagonist toward W-3.

TABLE 2

Analgesic agonist activity of 1-methyl(arylalkyl)-2-piperidylidene-2-sulfon(cyan)amide derivatives tested

| Substance | dose (mg/kg) | % inhibition |
|---|---|---|
| W-1 | 108.0 | 50 |
| W-2 | 68.0 | 50 |
| W-3 | 0.0038 | 50 |
| W-4 | 0.002 | 50 |
| W-5 | 2.4 | 50 |
| W-6 | 0.0028 | 50 |
| W-7 | 0.0028 | 50 |
| W-8 | 0.0018 | 50 |
| W-9 | 0.007 | 50 |
| W-10 | 0.0017 | 50 |
| W-11 | 0.00024 | 50 |
| W-12 | 1.2 | 50 |
| W-13 | 6.0 | 50 |
| W-14 | 0.00038 | 50 |
| W-15 | 0.007 | 50 |
| W-16 | 0.20 | 56 |
| W-17 | 0.20 | 65 |
| W-18 | 0.0000037 | 50 |
| W-19 | 0.000034 | 50 |
| 0-1 | 0.7 | 50 |
| Standards: | | |
| Aspirin (TM) | 50.0 | 50 |
| Dextropropoxyphene (TM) | 56.0 | 50 |
| Morphine Sulfate | 0.038 | 50 |

Compounds W-3, W-4, W-6, W-7, W-8, W-9, W-10, W-11, W-14, W-15, W-16 and W-17 are very active analgesics, being comparable to morphine sulfate.

TABLE 3

Analgesic agonist activity of 1-cyclopropylmethyl (cyclobutylmethyl,n-propyl,isobutyl,1-propenyl)-2-piperdylidene-2-sulfonamide derivatives which also exhibit analgesic antagonist activity

| Substance | Dose (mg/kg) | % Inhibition |
|---|---|---|
| W-20 | 2.3 | 50 |
| W-21 | 2.0 | 49 |
| W-22 | 2.0 | 50 |
| W-23 | 0.01 | 50 |
| W-24 | 0.20 | 61 |
| W-25 | 0.20 | 69 |
| W-26 | 1.4 | 50 |
| W-27 | 2.0 | 59 |
| W-28 | 2.0 | 82 |
| W-29 | 2.0 | 50 |
| W-30 | 2.0 | 59 |
| W-31 | 2.0 | 65 |
| W-32 | 0.013 | 50 |
| Standard: | | |
| Morphine sulfate | 0.038 | 50 |
| Aspirin (TM) | 50.0 | 50 |

Compounds W-20 to W-32 are all active analgesics which are much more potent than aspirin.

ANALGESIC ANTAGONIST TESTING

The analgesic antagonistic activity of compounds W-20 to W-32, inclusive, were determined by subcutaneous administration of the antagonists (W-20 to W-32) 10 min. prior to subcutaneous administration of the analgesic agonist (W-1 to W-19) as outlined in the procedure described for Analgesic Agonist Testing. Some results are illustrated below for the analgesic antagonist W-20 (Table 4). Similar results were obtained for other analgesic antagonists W-21 to W-32, inclusive.

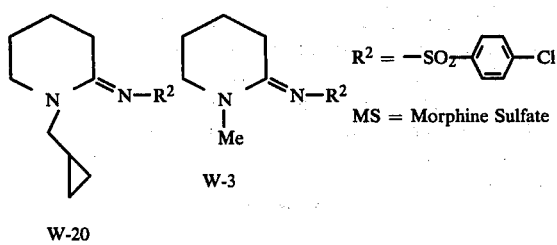

| DOSE (mg/kg sc) | W-20 (% Inhibn) | W-3 (% Inhibn) | MS (% Inhibn) |
|---|---|---|---|
| CONTROLS 0.2 | — | — | 90 |
| 0.5 | 36 | — | — |
| 2.0 | 46 | — | — |
| 2.0 | — | 97 | — |
| 5.0 | — | 100 | — |
| 10.0 | 69 | — | — |

TABLE 4

| | ANTAGONIST ACTIVITIES | | |
|---|---|---|---|
| Expt. No. | Dose of Antagonist (mg/kg sc) | Dose of Agonist (mg/kg sc) | % Inhibition |
| 1 | W-20 (2.0 mg/kg) | MS (0.2 mg/kg) | 55 (near complete block) |
| 2 | W-20 (10.0 mg/kg) | MS (0.2 mg/kg) | 66 (complete block) |
| 3 | W-20 (0.5 mg/kg) | W-3 (2.0 mg/kg) | 53 (partial block) |
| 4 | W-20 (2.0 mg/kg) | W-3 (2.0 mg/kg) | 49 (complete block) |
| 5 | Naloxone (1.0 mg/kg) | W-3 (5.0 mg/kg) | 45 (partial block) |

These results indicate that the analgesic antagonist W-20 (10 mg/kg sc) completely blocks the analgesic effect of morphine sulfate (0.2 mg/kg sc); that the analgesic antagonist W-20 (2.0 mg/kg sc) completely blocks the analgesic effect of W-3 (2.0 mg/kg sc) and that Naloxone (1.0 mg/kg sc) partially blocks the analgesic effect of W-3 (5.0 mg/kg sc).

We claim:

1. A 1-alkyl(arylalkyl,cycloalkylalkyl,alkenyl)-piperidylidene-2-sulfonamide or -2-cyanamide of the formula (1):

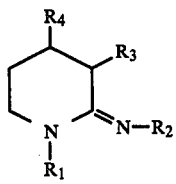

or a non-toxic pharmaceutically acceptable salt thereof, wherein $R_1$ is a lower alkyl, phenyl lower alkyl, amino substituted phenyl lower alkyl, nitro substituted phenyl lower alkyl, cycloloweralkyl lower alkyl or lower alkenyl substituent; $R_2$ are selected from the group consisting of cyano, pyridyl sulfonyl, lower alkyl substituted sulfonyl, phenylsulfonyl, lower alkoxy substituted phenylsulfonyl, halogen substituted phenylsulfonyl, nitro substituted phenylsulfonyl, amino substituted phenylsulfonyl and lower alkanoylamino substituted phenylsulfonyl; $R_3$ is a hydrogen or halogen atom; and $R_4$ is a hydrogen, lower alkyl or lower alkoxy substituent.

2. 1-methylpiperidylidene-2-methanesulfonamide, according to claim 1.

3. 1-methylpiperidylidene-2-benzenesulfonamide, according to claim 1.

4. 1-methylpiperidylidene-2-(4-chlorophenyl)sulfonamide, according to claim 1.

5. 1-methylpiperidylidene-2-(4-methoxyphenyl)sulfonamide, according to claim 1.

6. 1-methylpiperidylidene-2-(4-nitrophenyl)sulfonamide, according to claim 1.

7. 1-methylpiperidylidene-2-(3-nitrophenyl)sulfonamide, according to claim 1.

8. 1-methylpiperidylidene-2-(2-nitrophenyl)sulfonamide, according to claim 1.

9. 1-methylpiperidylidene-2-(4-aminopheyl)sulfonamide, according to claim 1.

10. 1-methylpiperidylidene-2-(3-aminophenyl)sulfonamide, according to claim 1.

11. 1-methylpiperidylidene-2-(2-aminophenyl)sulfonamide, according to claim 1.

12. 1-methylpiperidylidene-2-(4-acetamidophenyl)sulfonamide, according to claim 1.

13. 1-methylpiperidylidene-2-cyanamide, according to claim 1.

14. 1-methylpiperidylidene-2-(3-pyridyl)sulfonamide, according to claim 1.

15. 1-phenylethylpiperidylidene-2-(4-chlorophenyl)sulfonamide, according to claim 1.

16. 1-phenylethylpiperidylidene-2-(4-aminophenyl)sulfonamide, according to claim 1.

17. 1-phenylethylpiperidylidene-2-(3-pyridyl)sulfonamide, according to claim 1.

18. 1-(4-nitrophenylethyl)piperidylidene-2-(4-chlorophenyl)sulfonamide, according to claim 1.

19. 1-(4-aminophenyllethyl)piperidylidene-2-(4-chlorophenyl)sulfonamide, according to claim 1.

20. 3-bromo-1-methylpiperidylidene-2-cyanamide, according to claim 1.

21. 1,4-dimethylpiperidylidene-2-cyanamide, according to claim 1.

22. 4-ethoxy-1-methylpiperidylidene-2-cyanamide, according to claim 1.

23. 1-cyclopropylmethylpiperidylidene-2-(4-chlorophenyl)sulfonamide, according to claim 1.

24. 1-cyclopropylmethylpiperidylidene-2-(4-aminophenyl)sulfonamide, according to claim 1.

25. 1-cyclopropylmethylpiperidylidene-2-(3-pyridyl)sulfonamide, according to claim 1.

26. 1-cyclobutylmethylpiperidylidene-2-(4-chlorophenyl)sulfonamide, according to claim 1.

27. 1-cyclobutylmethylpiperidylidene-2-(4-aminophenyl)sulfonamide, according to claim 1.

28. 1-cyclobutylmethylpiperidylidene-2-(3-pyridyl)sulfonamide, according to claim 1.

29. 1-n-propylpiperidylidene-2-(4-chlorophenyl)sulfonamide, according to claim 1.

30. 1-n-propylpiperidylidene-2-(4-aminophenyl)sulfonamide, according to claim 1.

31. 1-n-propylpiperidylidene-2-(3-pyridyl)sulfonamide, according to claim 1.

32. 1-isobutylpiperidylidene-2-(4-chlorophenyl)sulfonamide, according to claim 1.

33. 1-isobutylpiperidylidene-2-(4-aminophenyl)sulfonamide, according to claim 1.

34. 1-isobutylpiperidylidene-2-(3-pyridyl)sulfonamide, according to claim 1.

35. E-1-(1-propenyl)piperidylidene-2-(4-chlorophenyl)sulfonamide, according to claim 1.

36. A composition comprising the compound of claim 1 in a pharmaceutical carrier, sufficient active compound being present so that the composition has analgesic-agonist or analgesic-antagonist activity.

37. The composition of claim 36, wherein the pharmaceutical carrier is a liquid carrier for injection.

38. The composition of claim 36, wherein the pharmaceutical carrier is a solid or suitable liquid for oral administration.

* * * * *